United States Patent
Dougherty (10) Patent No.: US 8,333,802 B2
(45) Date of Patent: Dec. 18, 2012

(54) SINGLE TUNNEL DOUBLE BUNDLE ANTERIOR CRUCIATE LIGAMENT RECONSTRUCTION

(76) Inventor: Christopher P. Dougherty, Rogers, AR (US)

(*) Notice: Subject to any disclaimer, the term of this patent is extended or adjusted under 35 U.S.C. 154(b) by 360 days.

(21) Appl. No.: 12/511,463

(22) Filed: Jul. 29, 2009

(65) Prior Publication Data

US 2010/0049319 A1   Feb. 25, 2010

Related U.S. Application Data

(60) Provisional application No. 61/097,460, filed on Sep. 16, 2008.

(51) Int. Cl.
*A61F 2/08* (2006.01)
(52) U.S. Cl. .............. 623/13.12; 623/13.17; 623/13.2
(58) Field of Classification Search ....... 623/13.11–13.2
See application file for complete search history.

(56) References Cited

U.S. PATENT DOCUMENTS

| | | | | |
|---|---|---|---|---|
| 4,712,542 A * | 12/1987 | Daniel et al. | ................. | 606/96 |
| 4,755,183 A * | 7/1988 | Kenna | ................. | 623/13.14 |
| 4,773,910 A * | 9/1988 | Chen et al. | ................. | 623/13.2 |
| 4,795,466 A * | 1/1989 | Stuhmer et al. | ................. | 623/13.2 |
| 4,804,383 A * | 2/1989 | Rey et al. | ................. | 623/13.11 |
| 4,863,471 A * | 9/1989 | Mansat | ................. | 623/13.2 |
| 4,950,271 A * | 8/1990 | Lewis et al. | ................. | 606/102 |
| 4,969,895 A * | 11/1990 | McLeod et al. | ................. | 606/96 |
| 5,004,474 A * | 4/1991 | Fronk et al. | ................. | 623/13.14 |
| 5,037,426 A * | 8/1991 | Goble et al. | ................. | 606/96 |
| 5,071,420 A * | 12/1991 | Paulos et al. | ................. | 606/99 |
| 5,078,745 A * | 1/1992 | Rhenter et al. | ................. | 623/13.12 |
| 5,263,984 A * | 11/1993 | Li et al. | ................. | 623/13.18 |
| 5,306,301 A * | 4/1994 | Graf et al. | ................. | 606/232 |
| RE34,762 E * | 10/1994 | Goble et al. | ................. | 606/96 |
| 5,507,750 A * | 4/1996 | Goble et al. | ................. | 606/102 |
| 5,562,669 A * | 10/1996 | McGuire | ................. | 623/13.12 |
| 5,630,820 A * | 5/1997 | Todd | ................. | 606/90 |
| 5,713,897 A * | 2/1998 | Goble et al. | ................. | 606/53 |
| 5,961,520 A * | 10/1999 | Beck et al. | ................. | 606/232 |
| 6,001,106 A * | 12/1999 | Ryan et al. | ................. | 606/102 |

(Continued)

OTHER PUBLICATIONS

Performance Orthopaedic Surgery & Sports Medicine. "Double Bundle ACL". Downloaded from <http://www.performanceorthosports.com/DOUBLEBUNDLEACL.html> on Nov. 17, 2011.*

(Continued)

*Primary Examiner* — David Isabella
*Assistant Examiner* — Andrew Iwamaye
(74) *Attorney, Agent, or Firm* — Husch Blackwell LLP; H. Frederick Rusche (57) ABSTRACT

The present invention provides a method of performing anterior cruciate ligament replacement. Specifically, a graft tissue is harvested from a patient and single tunnels are prepared in each of the tibia and the femur of the patient. The graft is secured in the femoral tunnel and separated into an anterior cruciate medial bundle and a anterior cruciate posterior lateral bundle. The bundles are inserted through the tibial tunnel. During insertion the posterior lateral bundle is positioned in a posterior lateral position in the tibial tunnel while the anterior cruciate medial bundle is positioned in an anterior cruciate medial position in the tibial tunnel. The anterior cruciate medial bundle is then tensioned while the patient's knee is in approximately 90 degrees of flexion, and the posterior lateral bundle is tensioned while the patient's knee is approximately in full extension. Each of the bundles is then secured in the tibial tunnel.

6 Claims, 6 Drawing Sheets

U.S. PATENT DOCUMENTS

| | | | |
|---|---|---|---|
| 6,056,752 A * | 5/2000 | Roger | 623/13.12 |
| 6,152,928 A * | 11/2000 | Wenstrom, Jr. | 606/232 |
| 6,171,310 B1 * | 1/2001 | Giordano et al. | 606/60 |
| 6,235,057 B1 * | 5/2001 | Roger et al. | 623/13.12 |
| 6,533,802 B2 * | 3/2003 | Bojarski et al. | 606/232 |
| 6,610,064 B1 * | 8/2003 | Goble et al. | 606/232 |
| 6,616,694 B1 * | 9/2003 | Hart | 623/13.14 |
| 6,623,524 B2 * | 9/2003 | Schmieding | 623/13.14 |
| 6,679,889 B1 * | 1/2004 | West et al. | 606/88 |
| 6,699,286 B2 * | 3/2004 | Sklar | 623/13.17 |
| 6,893,462 B2 * | 5/2005 | Buskirk et al. | 623/13.17 |
| 6,994,725 B1 * | 2/2006 | Goble | 623/13.14 |
| 7,118,578 B2 * | 10/2006 | West et al. | 606/88 |
| 7,137,996 B2 * | 11/2006 | Steiner et al. | 623/13.14 |
| 7,141,066 B2 * | 11/2006 | Steiner et al. | 623/13.12 |
| 7,144,424 B2 * | 12/2006 | Steenlage | 623/13.14 |
| 7,144,425 B2 * | 12/2006 | Steiner et al. | 623/13.14 |
| 7,160,285 B2 * | 1/2007 | Sklar et al. | 606/1 |
| 7,309,356 B2 * | 12/2007 | Steiner | 623/13.14 |
| 7,326,247 B2 * | 2/2008 | Schmieding et al. | 623/13.14 |
| 7,468,074 B2 * | 12/2008 | Caborn et al. | 623/13.14 |
| 7,485,136 B2 * | 2/2009 | Chan | 606/321 |
| 7,591,850 B2 * | 9/2009 | Cavazzoni | 623/13.11 |
| 7,637,910 B2 * | 12/2009 | Schmieding et al. | 606/80 |
| 7,686,810 B2 * | 3/2010 | West et al. | 606/88 |
| 7,713,293 B2 * | 5/2010 | Tucciarone et al. | 606/321 |
| 7,713,300 B2 * | 5/2010 | Meridew et al. | 623/13.14 |
| 7,736,364 B2 * | 6/2010 | Stone | 606/80 |
| 7,763,071 B2 * | 7/2010 | Bianchi et al. | 623/13.12 |
| 7,763,072 B2 * | 7/2010 | Bianchi et al. | 623/13.14 |
| 7,776,039 B2 * | 8/2010 | Bernstein et al. | 606/74 |
| 7,776,089 B2 * | 8/2010 | Bianchi et al. | 623/13.12 |
| 7,819,917 B2 * | 10/2010 | Schmieding et al. | 623/13.14 |
| 2001/0021875 A1 * | 9/2001 | Enzerink et al. | 623/13.17 |
| 2002/0013623 A1 * | 1/2002 | Sklar | 623/13.17 |
| 2002/0040241 A1 * | 4/2002 | Jarvinen | 623/13.14 |
| 2002/0161439 A1 * | 10/2002 | Strobel et al. | 623/13.14 |
| 2002/0188298 A1 * | 12/2002 | Chan | 606/72 |
| 2003/0167090 A1 * | 9/2003 | Chervitz et al. | 623/13.14 |
| 2003/0171810 A1 * | 9/2003 | Steiner | 623/13.14 |
| 2003/0171811 A1 * | 9/2003 | Steiner et al. | 623/13.17 |
| 2004/0059415 A1 * | 3/2004 | Schmieding | 623/13.12 |
| 2004/0199166 A1 * | 10/2004 | Schmieding et al. | 606/79 |
| 2004/0267362 A1 * | 12/2004 | Hwang et al. | 623/13.15 |
| 2005/0065533 A1 * | 3/2005 | Magen et al. | 606/102 |
| 2005/0096743 A1 * | 5/2005 | Schmieding et al. | 623/13.14 |
| 2005/0137704 A1 * | 6/2005 | Steenlage | 623/13.14 |
| 2005/0203621 A1 * | 9/2005 | Steiner et al. | 623/13.14 |
| 2005/0203623 A1 * | 9/2005 | Steiner et al. | 623/13.14 |
| 2006/0067971 A1 * | 3/2006 | Story et al. | 424/426 |
| 2006/0229722 A1 * | 10/2006 | Bianchi et al. | 623/13.14 |
| 2007/0225805 A1 * | 9/2007 | Schmieding | 623/13.14 |
| 2007/0239275 A1 * | 10/2007 | Willobee | 623/13.17 |
| 2007/0250067 A1 * | 10/2007 | Schmieding et al. | 606/96 |
| 2007/0270857 A1 * | 11/2007 | Lombardo et al. | 606/72 |
| 2008/0119929 A1 * | 5/2008 | Schmieding et al. | 623/13.14 |
| 2008/0228271 A1 * | 9/2008 | Stone et al. | 623/13.12 |
| 2008/0234819 A1 * | 9/2008 | Schmieding et al. | 623/13.14 |
| 2008/0300683 A1 * | 12/2008 | Altman et al. | 623/13.11 |
| 2009/0018654 A1 * | 1/2009 | Schmieding et al. | 623/13.14 |
| 2009/0228017 A1 * | 9/2009 | Collins | 606/96 |
| 2009/0234451 A1 * | 9/2009 | Manderson | 623/13.14 |
| 2010/0049258 A1 * | 2/2010 | Dougherty | 606/86 R |
| 2011/0040380 A1 * | 2/2011 | Schmieding et al. | 623/13.14 |

OTHER PUBLICATIONS

Caborn et al. "Single Femoral Socket Double-Bundle Anterior Cruciate Ligament Reconstruction Using Tibialis Anterior Tendon: Description of a New Technique". Arthroscopy: The Journal of Arthroscopic and Related Surgery, vol. 21, No. 10 Oct. 2005: pp. 1273.e1-1273.e8 1273.e1.*

Nyland et al. "Anatomical Double-Bundle Anterior Cruciate Ligament Reconstruction: Maximizing Benefits While Minimizing Complexity: A Balanced Potential Approach". Techniques in Knee Surgery (2007) 6: 191-203.*

Takeuichi et al. "Double-Bundle Anatomic Anterior Cruciate Ligament Reconstruction Using Bone-Hamstring-Bone Composite Graft". Arthroscopy: The Journal of Arthroscopic and Related Surgery, vol. 18, No. 5 May-Jun. 2002: pp. 550-555.*

Sakane et al. "In Situ Forces in the Anterior Cruciate Ligament and Its Bundles in Response to Anterior Tibial Loads". Journal of Orthopaedic Research (1997) 15: 285-293.*

Crawford et al. "Anatomic double bundle ACL reconstruction: a literature review". Knee Surg Sports Traumatol Arthrosc (2007) 15:946-964.*

* cited by examiner

SINGLE TUNNEL DOUBLE BUNDLE ANTERIOR CRUCIATE LIGAMENT RECONSTRUCTION

CROSS-REFERENCE TO RELATED APPLICATIONS

This application claims priority to U.S. Provisional Patent Application Ser. No. 61/097,460, which is herein incorporated in its entirety and is related to U.S. Provisional Patent Application Ser. No. 61/090,129, which is U.S. Patent Application TBD.

BACKGROUND OF THE INVENTION

1. Field of the Invention

The present invention provides a method for anterior cruciate ligament reconstruction and, more particularly, a method for single tunnel double bundle anterior cruciate ligament reconstruction.

2. Related Art

Single tunnel single bundle anterior cruciate ligament reconstruction (STSBACLR) has long been established as a method of anterior cruciate ligament (ACL) reconstruction. A variety of graft choices are available to surgeons during ACL reconstruction. These choices include autogenous patellar or quadriceps tendon with bone blocks, or hamstring tendons. In addition, changed here tendon allografts (from donors) may be used. The main portion of the ACL which needs to be reconstructed is the anterolateral bundles. Arthroscopic assisted or open ACL reconstructions involve removing the remaining native ACL and drilling a tunnel at the anatomic attachment site of the anterolateral or posterior medial bundle at the anterolateral wall of the intercondylar notch. This tunnel is drilled in line with the roof of the notch and about 1-3 mm from the posterior articular surface of the lateral femoral condyle. The tibial attachment site is then prepared by identifying the normal attachment site of the ACL at the bottom of the ACL facet. A tibial tunnel is drilled, at approximately a 60 coronal° angle and about 3-6 cm from the joint line, from anterior to posterior. Once the tunnels are drilled, sharp edges and soft tissues around the tunnel exit site are smoothed off with the use of a rasp. The graft is then passed into the joint and fixed in its femoral tunnel (usually with an interference screw). The graft is then tensioned distally while the knee is cycled several times to remove any slack in the graft. The graft is fixed to the tibia, usually with staples, while the knee is flexed 15-30°, distal traction is placed on the graft, and a posterior force is applied to the tibia. After fixation, the anterior cruciate drawer is assessed to verify a return of normal anterior stability to the knee, and the surgical incisions are closed.

Double bundle double tunnel anterior cruciate ligament reconstruction (DBDTACLR) has recently been described as a technique for ACL reconstruction which provides two bundles of tissue in separate tunnels. Recent biomechanical studies have shown that an anatomic double-bundle ACL reconstruction is superior in restoring normal knee laxity compared with the conventional single-bundle isometric reconstruction. One technique uses a double-bundle Y-shaped hamstring tendon graft. A double- or triple-bundle semitendinosus-gracilis tendon graft is utilized and directly fixed with interference screws. In the lateral femoral condyle, two femoral tunnels are created inside-out through a low anterolateral arthroscopic portal. First, in full extension, the double-stranded gracilis graft is fixed with an interference screw inside the lower femoral socket, representing the insertion site of the posterolateral bundle. In 90 degrees of flexion the combined semitendinosus-gracilis graft is pretensioned and fixed inside the upper femoral socket. Alternatively the graft is placed into the a single femoral tunnel and an interference screw simply placed between the grafts without respect for control of rotation and position of the graft to simulate true orientation of the grafts into anteromedial and posteriolateral bundles. The tendon is inserted in the tibial tunnel. Finally, pretension is applied to the bundles in extension and another screw is inserted. Alternatively two separate tibial tunnels are utilized and the separate anteromedial and posterolateral tunnels and fixed with staples or screws. Using this technique, the stronger semitendinosus part of the double-bundle graft, which mimics the anterolateral bundle of the ACL, is fixed in full extension, whereas the smaller gracilis tendon part (posteromedial bundle) is fixed in flexion.

Kinematically the double bundle anterior cruciate ligament reconstruction has shown itself to be more closely related to the actual normal motion of the knee when compared to single bundle anterior cruciate ligament reconstructions. DBDTA-CLR is technically demanding procedure requiring an extremely high level of surgeon skill. In addition DBDTA-CLR requires four separate fixation devices to secure the soft tissue bundles in place to recreate a torn anterior cruciate ligament. Each bundle of tissue is separately tensioned in the respective tunnel prior to fixation with orthopedic devices.

SUMMARY OF THE INVENTION

The present invention provides a novel technique in which a double bundle ACL reconstruction is performed through a single tunnel and the separate bundles are independently tensioned. Accordingly, a new type of ACL reconstruction the Single Tunnel Double Bundle Anterior Cruciate Ligament Reconstruction (STBDACLR) is created.

STDBACLR utilizes a standard graft harvest and can be performed using either allograft or autograft tissues such as bone patellar tendon bone, wherein the graft includes a portion of the patellar tendon having a bone plug on each end, or semitendinosus gracilis (hamstring) tendons. Standard tibial and femoral tunnels are prepared using either a trans-tibial or a trans-portal technique. The femoral graft fixation is important because the bundles for the ACL must be oriented in a proper direction to provide separate kinematic bundles created a through a single tunnel. The graft position on the femoral side is held in place through screws and/or other fixation devices used where the graft is prepared and separated into two separate bundles through implant design or through surgeon preparation. When using hamstring grafts, the grafts are positioned on the femoral side to provide for a posterior cruciate bundle that can be independently tensioned after femoral tunnel fixation. When using bone patellar tendon bone grafts, the femoral bone plug is left as one piece when inserted and the graft is prepared to provide for the separate bundles in the tibia.

During graft introduction into the knee two kinematically separate bundles are created. As the graft is pulled into the knee, the surgeon, who has marked the appropriate bundle of tissue which is to be the posterior cruciate lateral bundle, rotates this bundle to the anterior cruciate posterior lateral position in the tibia while rotating the other bundle, the anterior cruciate medial bundle, to the anterior cruciate medial portion of the tibial tunnel, thereby creating the soft tissue required for both the anterior cruciate posterior lateral and anterior cruciate medial bundles. With the separate bundle created in the knee and appropriately oriented, the bundles are tensioned independently. The anterior cruciate medial bundle is tensioned with the knee in 90 degrees of flexion while the anterior cruciate posterior lateral bundle is tensioned with the knee in full extension. An external tensioning device is capable of cycling the separate bundles under tension or this can be accomplished with two separate screws inserted as posts into the tibia. Once the graft is tensioned, tibial fixation is either completed with the screws alone or, using a removable tensioning device, the bundles are secured in the tibial tunnel with a screw type fixation device and the external tensioner is removed. By anatomically creating two separate bundles and kinematically tensioning those separate bundles and fixating them, the surgeon creates a single tunnel double bundle anterior cruciate ligament repair (STDBACLR).

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

FIGS. 1-7 illustrate a method of reconstructing the anterior cruciate ligament (ACL) of the knee 11 using a single tunnel double bundle technique. Prior to the reconstruction a standard graft harvest is performed using either allograft or autograft tissues such as bone patellar tendon bone or semitendinosus gracilis (hamstring) tendons. Standard tibial and femoral tunnels then are prepared using either a trans-tibial or a trans-portal technique.

Figure 1:
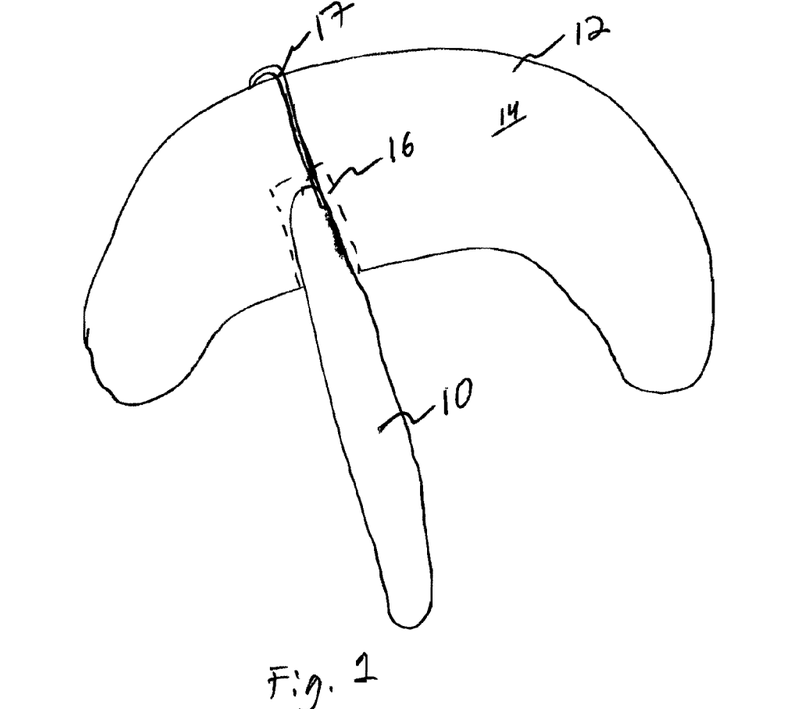
FIG. 1 is a view of a graft inserted into the femur of a knee.
Figure 2:
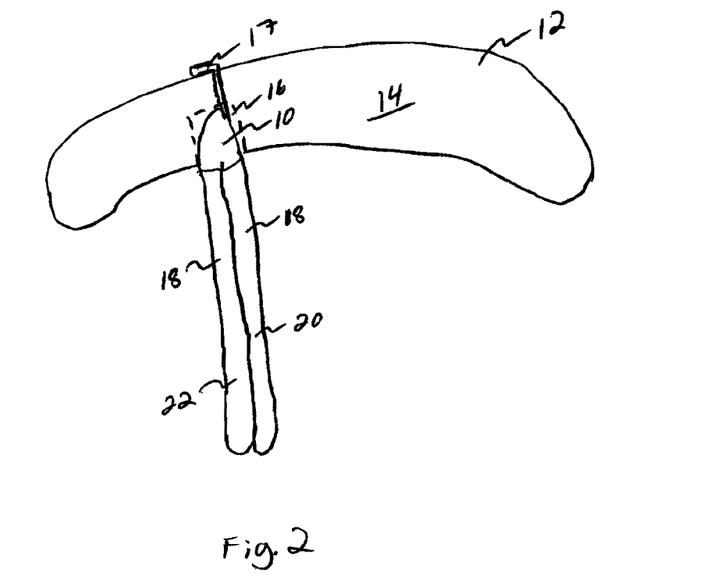
FIG. 2 is a view of the graft shown in FIG. 1 separated into two bundles.
Figure 8:
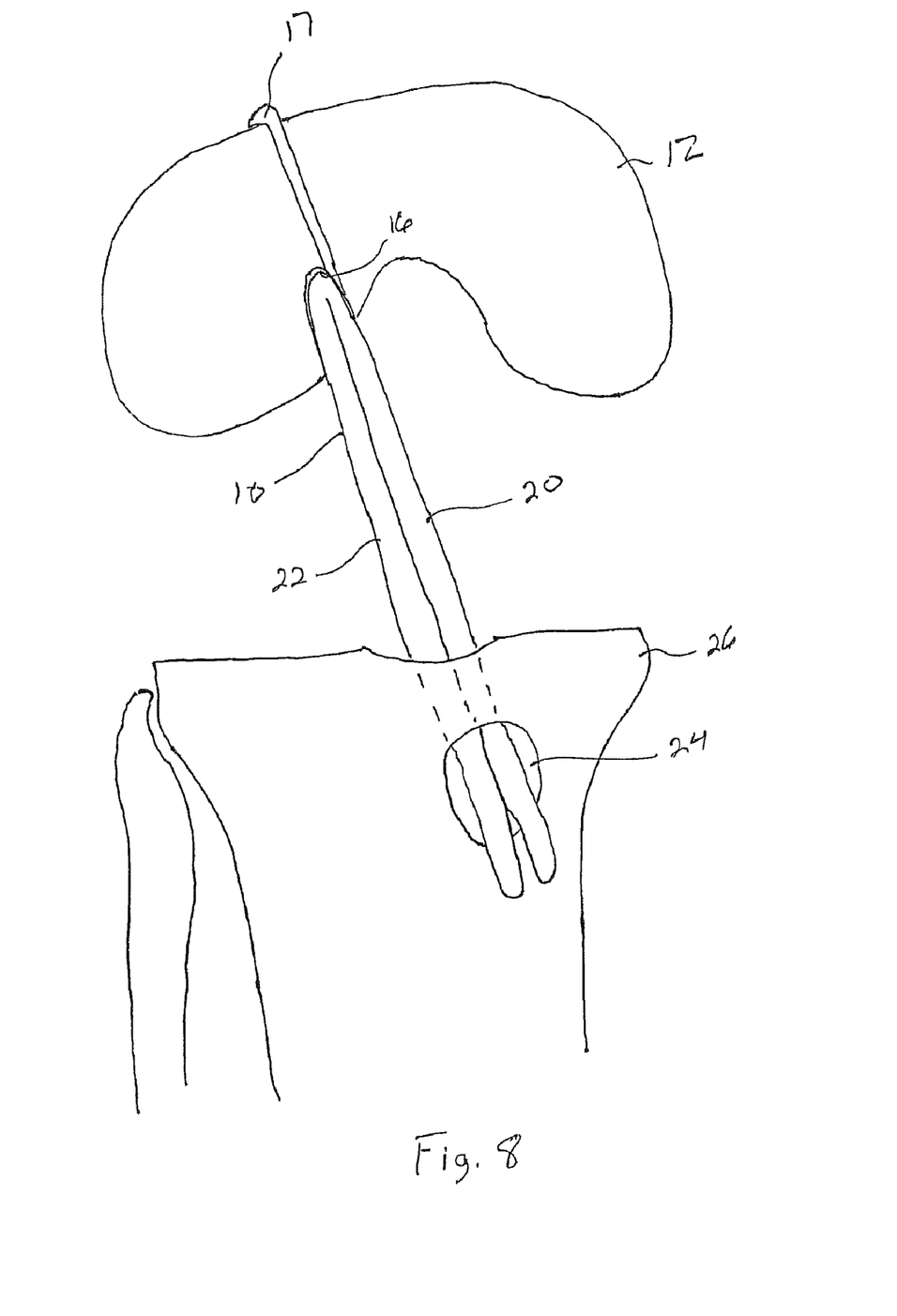
FIG. 8 is a view of a graft inserted into the femur of knee according to another embodiment of the present invention.

As shown in FIG. 1, the graft 10 is fixed in the femur 12 using standard fixation techniques. For example, in the exemplary embodiment the graft 10 is positioned on the femoral side 14 to provide for an anterior cruciate bundle that can be independently tensioned after femoral tunnel fixation. When using hamstring grafts, the graft is configured to provide separate bundles, as shown in FIG. 8. Alternatively, when using bone patellar tendon bone grafts, the femoral bone plug is left as one piece when inserted and the graft is, prepared to provide for the separate bundles in the tibia as shown in FIGS. 1-2. The graft is fixed in the femoral tunnel 16 so that the bundles for the ACL are oriented in a proper direction to provide separate kinematic bundles created through a single tunnel. In the exemplary embodiment, the graft 10 is held in place on the femoral side 14 using screws and/or other fixation devices 17 used when the graft is prepared and separated into two separate bundles through implant design or through surgeon preparation.

Figure 3:
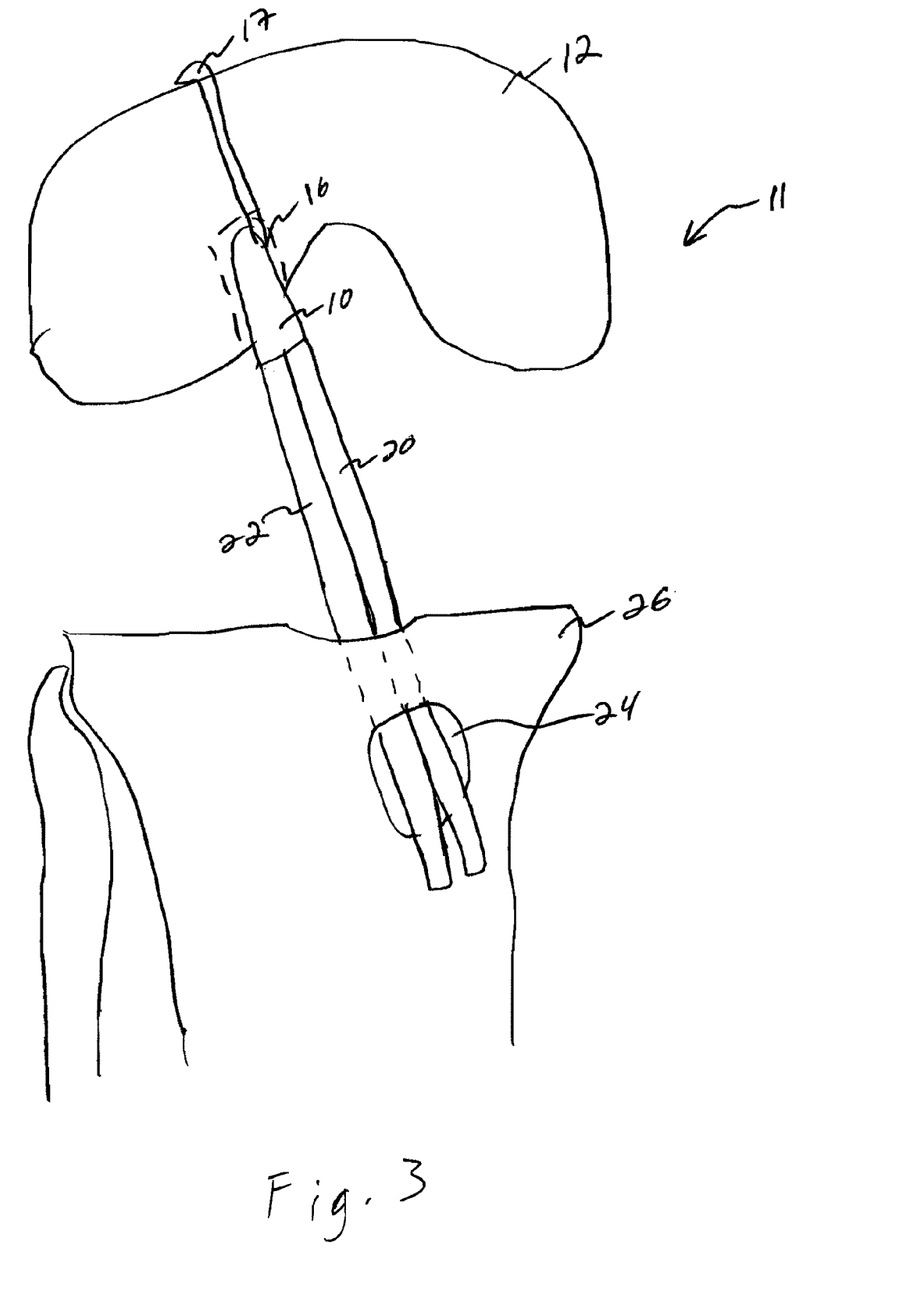
FIG. 3 is a view of the two bundles shown in FIG. 2 inserted through the tibia of the knee.
Figure 4:
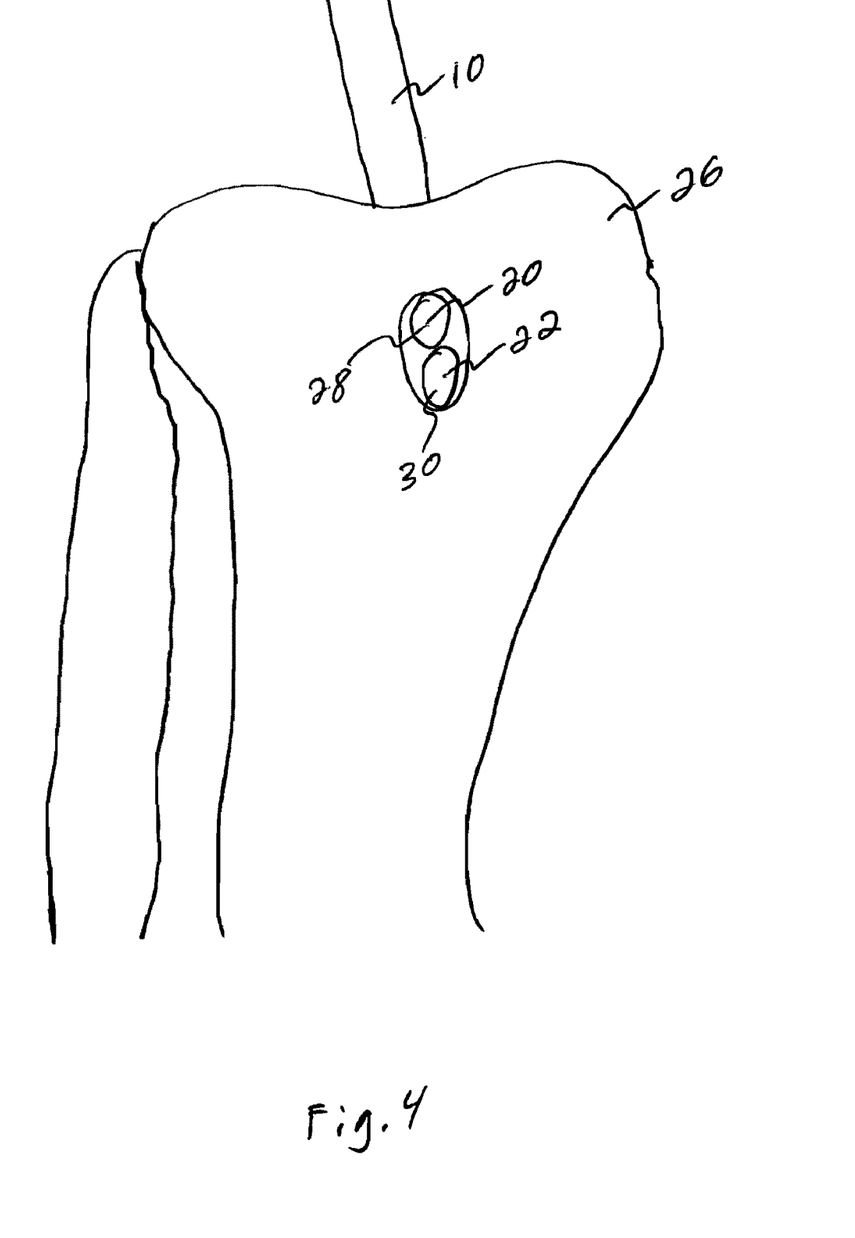
FIG. 4 is a view of the two bundles shown in FIG. 3 arranged as a posterior cruciate lateral bundle and anterior cruciate medial bundle.

As shown in FIG. 2, the graft 10 is separated into two kinematically separate bundles 18 after the graft 10 is introduced into the femur 12. Each bundle 18 is marked as either the anterior cruciate posterior lateral bundle 20 or the anterior cruciate medial bundle 22 and pulled through a tibial tunnel 24 formed in the tibia 26, as shown in FIG. 3. As shown in FIG. 4, as the graft is pulled through the tibial tunnel 24, the surgeon rotates the bundle labeled anterior cruciate posterior lateral bundle 20 into the posterior cruciate lateral position 28, and rotates the bundle labeled anterior cruciate medial bundle 22 into the anterior cruciate medial position 30, thereby creating the soft tissue required for both the anterior cruciate posterior lateral bundle 20 and anterior cruciate medial bundle 22.

Figure 5:
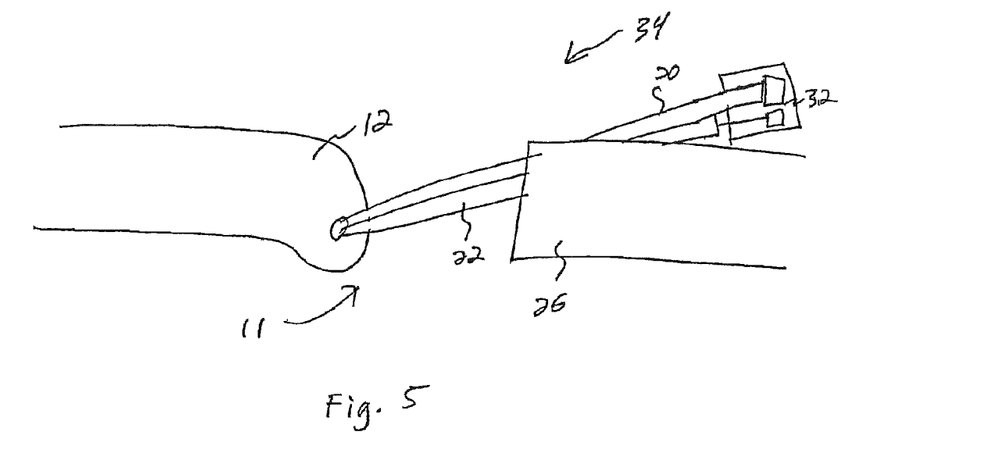
FIG. 5 is a view of the knee in extension to provide tension to the posterior cruciate lateral bundle shown in FIG. 4 using a tensioning device.
Figure 6:
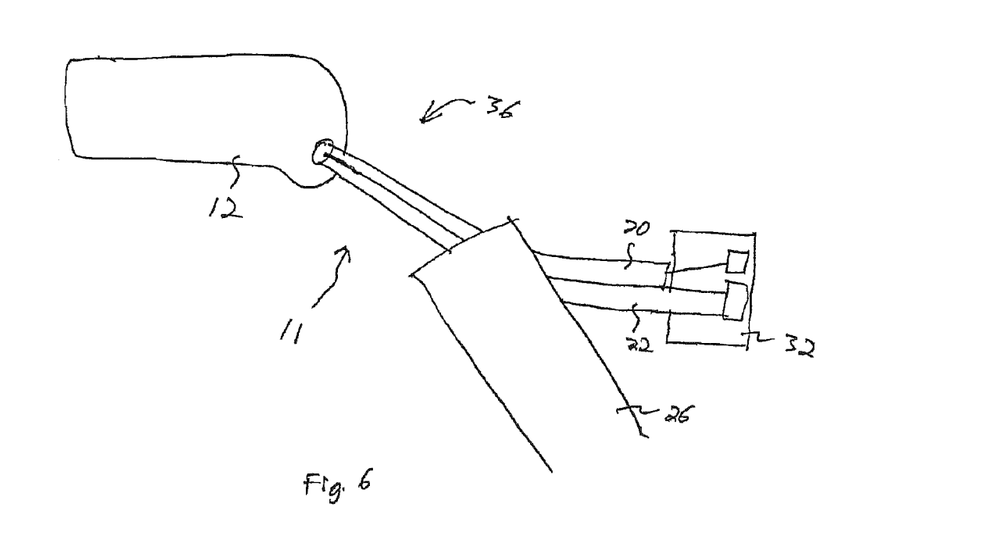
FIG. 6 is a view of the knee in flexion to provide tension to the anterior cruciate medial bundle shown in FIG. 4 using the tensioning device shown in FIG. 5.

With the anterior cruciate posterior lateral bundle 20 and the anterior cruciate medial bundle 22 created in the knee and appropriately oriented, the bundles 20 and 22 are tensioned independently using a tensioning device 32 that couples to each bundle 20 and 22. As seen in FIG. 5, the anterior cruciate posterior lateral bundle 20 is tensioned with the knee 11 in a first position 34 of approximately full extension. As will be appreciated by one of skill in the art, the knee is extended to at or near full extension. Specifically, while in this first position 34, the tensioning device 32 applies tension to the anterior cruciate lateral bundle 20 while the anterior cruciate medial bundle 22 is left in an untensioned position. As shown in FIG. 6, the knee 11 is then flexed into a second position 36 so that there is approximately 90 degrees of flexion between the femur 12 and the tibia 26. As will be appreciated by one of skill in the art, the knee is flexed to at or near 90 degrees. While in this second position 36, the tensioning device 32 applies tension to the anterior cruciate medial bundle 22 while the anterior cruciate lateral bundle 20 is left in an untensioned position. In one embodiment, the external tensioning device 32 cycles the separate bundles 20 and 22 under tension as the knee 11 is moved between the first position 34 and the second position 36. Alternatively, two separate screws are inserted as posts in the tibia 26 to individually secure the bundles 20 and 22 so that tensioning of the bundles 20 and 22 is performed without the tensioning device 32 by moving the knee 11 between the first position 34 and the second position 36.

Figure 7:
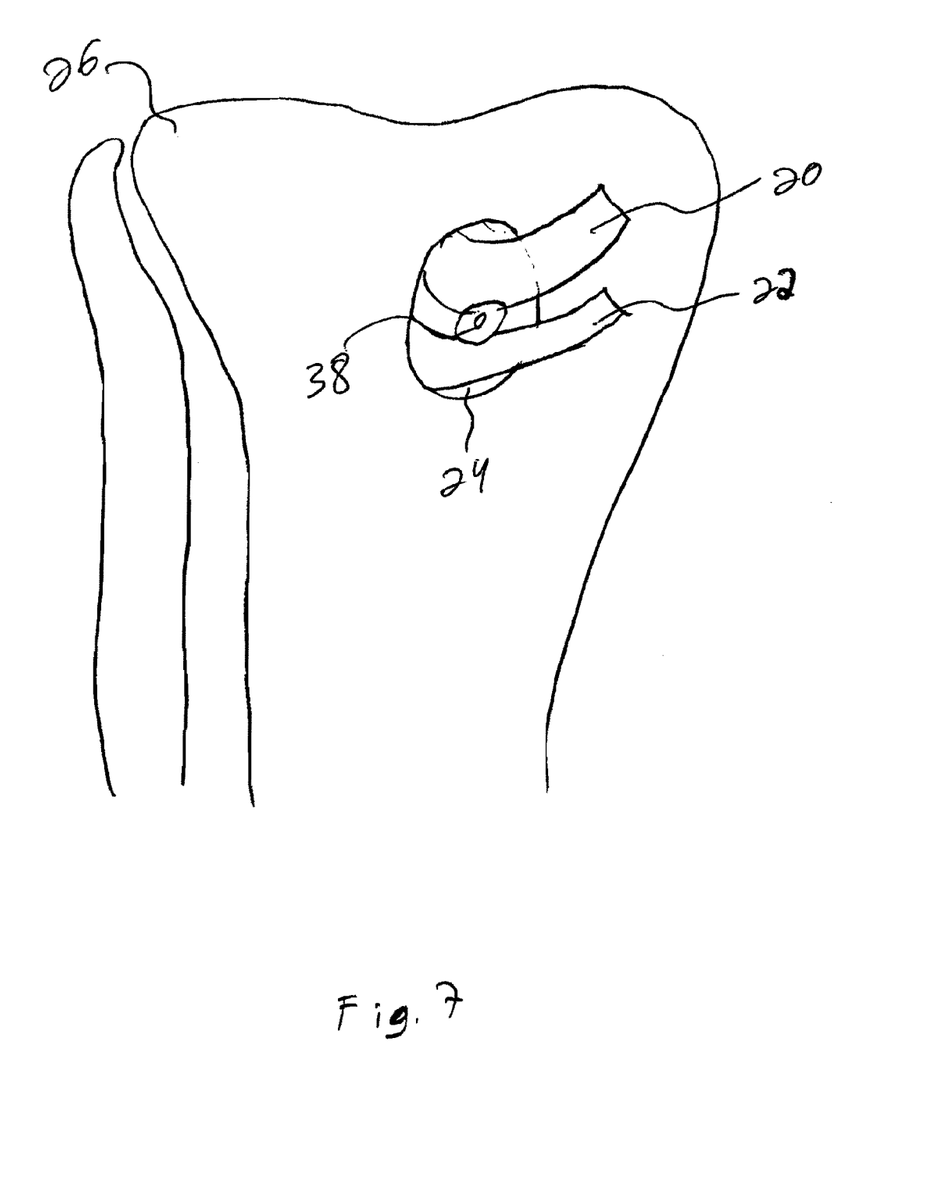
FIG. 7 is a view of the posterior cruciate lateral bundle and anterior cruciate medial bundle shown in FIG. 4 secured to the tibia shown in FIG. 3.

FIG. 7 illustrates tibial fixation of the anterior cruciate lateral bundle 20 and the anterior cruciate medial bundle 22 with a screw 38. The fixation is performed after the graft 10 has been tensioned and before the tensioning device 32 has been removed. In an alternative embodiment, the tensioning device 32 is used to secure the bundles 20 and 22 with any screw type fixation device. In other embodiments, alternative fixation devices may be used to secure the bundles 20 and 22. After the bundles 20 and 22 are secured to the tibia 26, the surgical wound is closed using standard techniques.

Accordingly, the above described invention enables the creation of two separate bundles using a single graft that is positioned using a single tunnel. The single tunnel enables a less invasive operation than known methods of replacing an anterior cruciate ligament. Moreover, the present invention enables the kinematic tensioning of separate bundles thereby providing a more effective and successful ligament replacement As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method of replacing an anterior cruciate ligament of a patient, said method comprising the steps of:
   preparing a bone patellar tendon bone graft having a first end and a second end, the second end having a bone plug;
   preparing a single femoral tunnel in a femur of the patient and a single tibial tunnel in a tibia of the patient;
   securing the bone plug in the femoral tunnel;
   subsequently leaving the bone plug as one piece while separating the the first end of the graft into a first bundle and a second bundle, such that the first bundle and second bundle are kinematically separate bundles at the first end;
   positioning the first bundle and second bundle in the tibial tunnel;
   rotating the first bundle into an anterior cruciate medial position in the tibial tunnel and rotating the second bundle into an anterior cruciate lateral position in the tibial tunnel prior to independently tensioning the first and second bundles;
   independently tensioning the first and second bundles prior to securing the first end of the graft; and
   securing both the first bundle and the second bundle of the first end of the graft in the tibial tunnel.

2. A method as recited in claim 1, further comprising tensioning the first and second bundle with a tensioning device coupled to the first and second bundle.

3. A method as recited in claim 1 further comprising tensioning the first bundle while the patient's knee is in 90 degrees of flexion prior to securing the first bundle.

4. A method as recited in claim 1 further comprising tensioning the second bundle while the patient's knee is in full extension prior to securing the second bundle.

5. A method of replacing an anterior cruciate ligament, said method comprising:
   harvesting a bone patellar tendon bone graft from a patient, the bone patellar tendon bone graft having a first end and a second end, the second end having a bone plug;
   preparing a single tibial tunnel in a tibia of the patient and a single femoral tunnel in a femur of the patient;
   securing the bone plug in the femoral tunnel;
   subsequently leaving the bone plug as one piece while separating the first end of the graft into an anterior cruciate medial bundle and an anterior cruciate lateral bundle, such that the anterior cruciate medial bundle and the anterior cruciate lateral bundle are kinematically separate from each other at the first end;
   inserting the anterior cruciate medial bundle and the anterior cruciate lateral bundle in the tibial tunnel;
   rotating the anterior cruciate lateral bundle in an anterior cruciate lateral position in the tibial tunnel and rotating the anterior cruciate medial bundle in an anterior cruciate medial position in the tibial tunnel prior to independently tensioning the anterior cruciate medial bundle and the anterior cruciate lateral bundle;
   independently tensioning the anterior cruciate medial bundle while the patient's knee is at 90 degrees of flexion and independently tensioning the anterior cruciate lateral bundle while the patient's knee is at full extension prior to securing the anterior cruciate medial bundle and the anterior cruciate lateral bundle in the tibial tunnel;
   securing the anterior cruciate medial bundle and the anterior cruciate lateral bundle in the tibial tunnel.

6. A method as recited in claim 5, wherein tensioning the anterior cruciate medial bundle and tensioning the anterior cruciate lateral bundle further comprises tensioning the anterior cruciate medial bundle and the anterior cruciate lateral bundle with a tensioning device coupled to the anterior cruciate medial bundle and the anterior cruciate lateral bundle.

\* \* \* \* \*